US009955929B2

(12) United States Patent
Huang et al.

(10) Patent No.: US 9,955,929 B2
(45) Date of Patent: May 1, 2018

(54) BITE TRAY HAVING FIDUCIAL MARKERS FOR HEAD SCAN REGISTRATION AND METHOD OF USE (71) Applicants: Jerry T. Huang, City of Industry, CA (US); Ta-Ko Huang, Kaohsiung (TW)

(72) Inventors: Jerry T. Huang, City of Industry, CA (US); Ta-Ko Huang, Kaohsiung (TW)

(*) Notice: Subject to any disclaimer, the term of this patent is extended or adjusted under 35 U.S.C. 154(b) by 0 days. days.

(21) Appl. No.: 15/403,096

(22) Filed: Jan. 10, 2017

(65) Prior Publication Data
US 2017/0196521 A1 Jul. 13, 2017

Related U.S. Application Data (62) Division of application No. 15/146,366, filed on May 4, 2016, now Pat. No. 9,554,869.
(Continued)

(51) Int. Cl.
*A61C 1/00* (2006.01)
*A61C 3/00* (2006.01)
(Continued)

(52) U.S. Cl.
CPC ............. *A61B 6/145* (2013.01); *A61B 5/055* (2013.01); *A61B 6/032* (2013.01); *A61C 1/082* (2013.01);
(Continued)

(58) Field of Classification Search
CPC .... A61B 2090/3995; A61B 2090/3916; A61B 2090/3954; A61B 2090/3966;
(Continued)

(56) References Cited

U.S. PATENT DOCUMENTS 4,618,978 A 10/1986 Cosman
5,769,861 A 6/1998 Vilsmeier
(Continued)

FOREIGN PATENT DOCUMENTS

DE 19619761 A1 11/1996
GB 2213066 A 8/1989

OTHER PUBLICATIONS

R.Ewers et al., Basic research and 12 years of clinical experience in computer assisted navigation technology, Int. J. Oral Maxillofac Surg., 2005; 1-8; 34, Elsevier Ltd., AUT.

*Primary Examiner* — Matthew Nelson
(74) *Attorney, Agent, or Firm* — Lawrence S. Cohen; Timothy T. Tyson (57) ABSTRACT The present invention is directed to a bite tray having fiducial markers for head scan registration and method of use. The bite tray is held by a patient in his teeth while the scan of his head and the fiducial markers is made by x-ray, CT, or MRI and the scan is entered into a computer to register the scan to the fiducial markers. Instrument optical markers are placed on a dental instrument and it is observed by a camera and the observation is entered into the computer to register the instrument optical markers to the dental instrument. Patient optical markers are placed on the patient and it is observed by the camera and the observation is entered into the computer to register the patient optical markers to the patient. The tip of the dental instrument is then touched to one of the fiducial markers making the location of the tip and the fiducial marker the same. The computer then registers the scan to the instrument and the patient. The bite tray is then removed from the mouth allowing access by the dentist to the teeth. The camera follows the movement of the instrument optical markers to
(Continued)

the patient optical markers to create a display of the instrument and tip on the scan.

1 Claim, 12 Drawing Sheets

Related U.S. Application Data (60) Provisional application No. 62/276,434, filed on Jan. 8, 2016.

(51) Int. Cl.
*A61B 6/14* (2006.01)
*A61B 5/055* (2006.01)
*A61B 6/03* (2006.01)
*A61C 1/08* (2006.01)
*A61C 3/02* (2006.01)
*A61C 9/00* (2006.01)
*A61B 90/00* (2016.01)

(52) U.S. Cl.
CPC .............. *A61C 3/02* (2013.01); *A61C 9/0006* (2013.01); *A61B 2090/3912* (2016.02); *A61B 2090/3916* (2016.02); *A61B 2090/3954* (2016.02); *A61B 2090/3966* (2016.02); *A61B 2090/3983* (2016.02); *A61B 2090/3995* (2016.02)

(58) Field of Classification Search
CPC .... A61B 2090/3983; A61B 2090/3912; A61B 6/145; A61B 6/032; A61B 5/055; A61C 9/0006; A61C 1/082
USPC .......................................................... 433/29
See application file for complete search history.

(56) References Cited

U.S. PATENT DOCUMENTS

| | | |
|---|---|---|
| 5,947,981 A | 9/1999 | Cosman |
| 6,223,067 B1 | 4/2001 | Vilsmeier |
| 6,978,167 B2 | 12/2005 | Dekel et al. |
| 8,226,651 B2 | 7/2012 | Gill et al. |
| 8,238,631 B2 | 8/2012 | Hartmann et al. |
| 9,084,535 B2 | 7/2015 | Girkin et al. |
| 2002/0095081 A1* | 7/2002 | Vilsmeier ................ A61B 6/12 600/407 |
| 2008/0171305 A1* | 7/2008 | Sonenfeld ............. A61C 1/084 433/215 |
| 2009/0209852 A1* | 8/2009 | Mate ..................... A61B 90/16 600/431 |
| 2010/0305580 A1 | 12/2010 | Henderson et al. |
| 2011/0052008 A1 | 3/2011 | Holsing et al. |
| 2011/0217667 A1* | 9/2011 | Groscurth ............. A61C 9/004 433/68 |
| 2013/0322719 A1 | 12/2013 | Dekel et al. |
| 2014/0364725 A1* | 12/2014 | Makower ............ A61B 5/6851 600/424 |
| 2015/0230901 A1* | 8/2015 | Hart ..................... A61C 19/04 433/29 |
| 2016/0030132 A1* | 2/2016 | Cheung ................. A61C 1/082 602/42 |
| 2016/0106517 A1* | 4/2016 | Groscurth ............. A61C 9/004 433/75 |
| 2016/0157967 A1* | 6/2016 | Kim .................. A61C 13/0004 433/201.1 |
| 2016/0184050 A1* | 6/2016 | Chodorow ........... A61B 5/0013 433/27 |
| 2016/0235483 A1* | 8/2016 | Zeilhofer ................ A61C 3/02 |

* cited by examiner

BITE TRAY HAVING FIDUCIAL MARKERS FOR HEAD SCAN REGISTRATION AND METHOD OF USE

CROSS REFERENCE TO RELATED APPLICATION

This application is a Divisional application and claims the filing benefit of Non-provisional application Ser. No. 15/146,366 filed May 4, 2016, and Provisional Application No. 62/276,434, filed Jan. 8, 2016, which are incorporated herein by reference.

TECHNICAL FIELD

The present invention pertains generally to head scanning procedures, and more particularly to a bite tray having fiducial markers for registration of head scans and method of use for guiding an instrument during head surgery.

BACKGROUND OF THE INVENTION

Surgical navigation systems using computers and monitors that register the locations of surgical instrument in relation to the patient are known in the art. An article titled "Basic research and 12 years of clinical experience in computer-assisted navigation technology: a review" by R. Ewers, et al. shows a setup for operating on a dental patient using an infrared camera to monitor tracking sensors attached to a surgical instrument and the head of the patient. Fiducial markers are placed on the patient before the CT scan is made. The tracking system picks up the positions of the patient and the surgical instrument and transfers them to a computer for registration.

Figure 1:
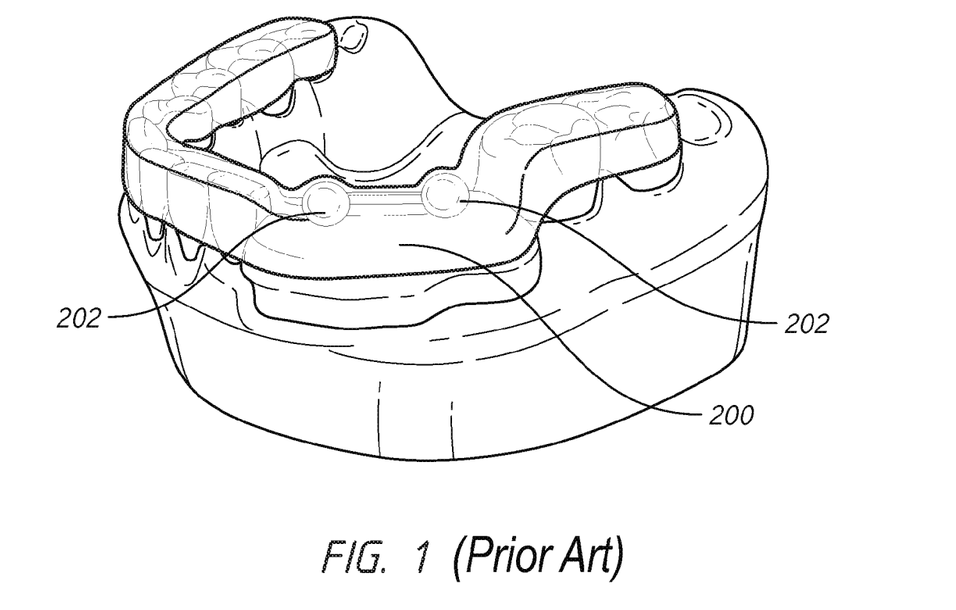
FIG. 1 is a perspective view of a prior art template for holding reference ceramic balls in place for a scan of the jaw.
Figure 2:
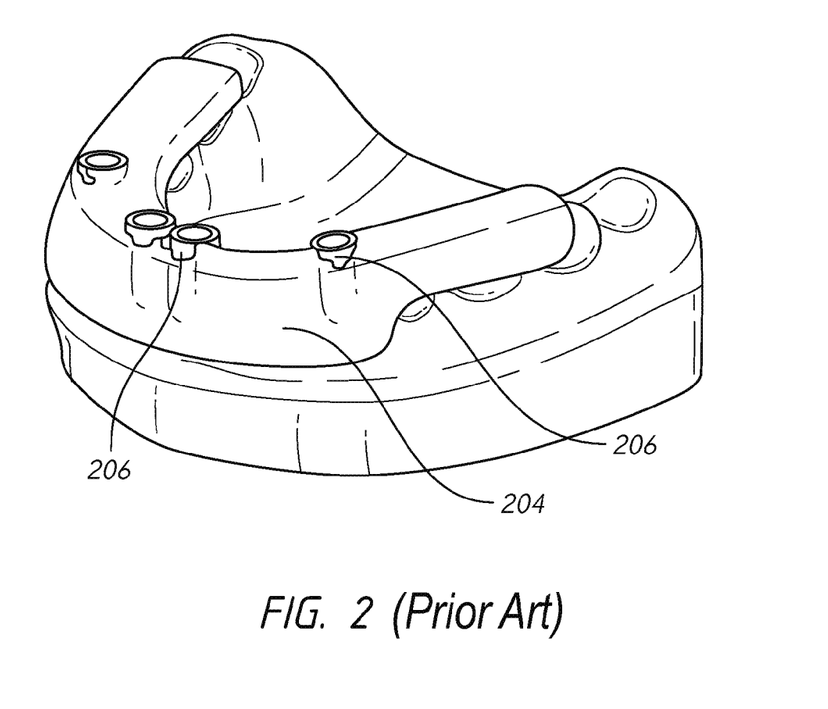
FIG. 2 is a perspective view of a prior art template for holding reference pins in place for a scan of the jaw.

FIG. 1 shows a prior art template 200 for use in dental implant surgery. Reference ceramic balls 202 are positioned over the desired positions for the implants. The balls are held in position for the scan by the vacuum formed template. FIG. 2 shows another prior art vacuum formed template 204 with pins 206 representing the proposed implant locations held in place at the desired locations. The x-ray or CT scan is then made and the results are used for planning purposes with respect to bone availability and mucosal thickness. The exact implant positions, diameters, and lengths can be determined. The templates are then removed for any actual oral surgery. No real time review and planning is possible using these fixtures.

A system for registering scans of the head and display of instruments on the scans in real time would be an advantage to oral and other surgeons.

BRIEF SUMMARY OF THE INVENTION

The present invention is directed to a bite tray having fiducial markers for registering scans of the head of a patient and method of use. The bite tray is positioned between the teeth of a patient. An inside teeth perimeter ridge is inside of the teeth and an outside teeth perimeter ridge is outside the teeth. Fiducial markers are positioned in fiducial marker holders outside of the outside teeth ridge. A settable compound is put in the bite tray. The patient bites into the settable compound making impressions of the teeth. The bite tray is then removed allowing the settable compound to set. The bite tray with the permanent impressions is then reinserted between the teeth and a x-ray, CT, or MRI scan is made of the head of the patient. The fiducial markers appear on the scan allowing the orientation of the scan to be registered on a data processing device and displayed. The instrument that is to be used for a procedure has an operating tip and instrument optical or magnetic markers. It is detected by a spatial tracking device such as an optical camera, infrared camera, or magnetic sensor and the data is sent to the data processing device to register the relationship of the operating tip to the markers on the instrument. Patient optical or magnetic markers are mounted on the patient's head away from the jaw. When the operating tip of the instrument is touched to a fiducial marker in the bite tray, the spatial tracker observes the instrument markers and patient markers and transmits the data to the data processing device. The data processing devices uses the data to compute and register the relationships of the instrument and patient optical or magnetic markers to the scan image of the patient's head and displays the computed image of the instrument superimposed on the scan image. The bite tray is then removed from the patient. When the head or oral surgeon moves the instrument, the spatial tracker observes the instrument markers and the patient markers and transmits the data to the data processing device. The data processing device computes the relationship between the current position of the operating tip based on the current positions of the instrument and patient optical or magnetic markers and displays the computed image of the operating tip and instrument in the new position superimposed on the scan image of the head for monitoring by the head or oral surgeon.

In an embodiment, the patient markers are attached to the top of the head of the patient and the bite tray is removed for work on the upper jaw. The patient can then open his jaw and the operating tip of the instrument is moved by the oral surgeon for work on the upper jaw. The positions of the instrument markers and patient markers are continuously observed by the spatial tracker and delivered to the data processing device. The data processing device uses the data to present an image of the instrument with the operating end superimposed on the scan of the head of the patient.

In another embodiment, the patient markers are attached to the lower jaw of the patient for procedures on the lower jaw. After the impressions are made in the bite tray, the bite tray is left on the lower jaw and the lower jaw is lowered for the x-ray, CT, or MRI scan. The bite tray is then removed for work on the lower jaw.

In yet another embodiment, the patient markers are attached to the side of the head of the patient for procedures on the head. After the x-ray, CT, or MRI scan is made of the head with the bite tray in place, the bite tray is removed for procedures on the head. The patient can then open his jaw for insertion of instruments into the mouth or anesthesia apparatus over the nose and mouth.

Other embodiments, in addition to the embodiments enumerated above, will become apparent from the following detailed description, taken in conjunction with the accompanying drawings that illustrate, by way of example, the principles of the bite registration device and method of use.

DETAILED DESCRIPTION OF THE INVENTION

Figure 3:
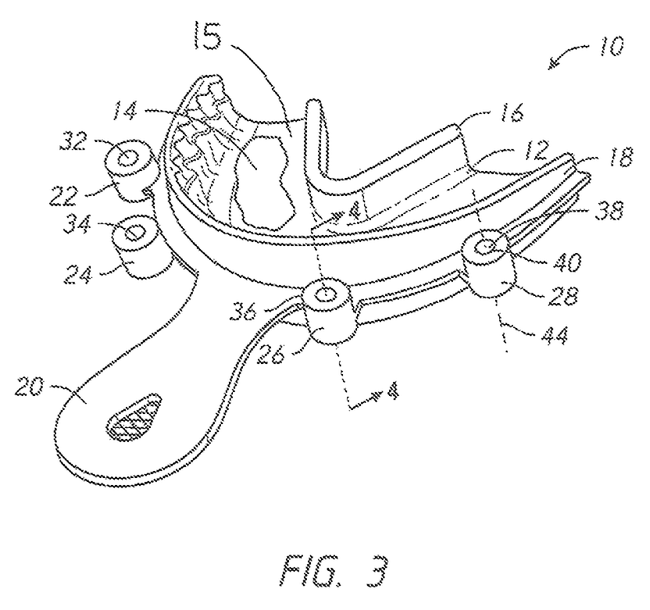
FIG. 3 illustrates a bite tray having fiducial markers in fiducial marker holders outside the outer teeth perimeter and a settable compound inside.
Figure 4:
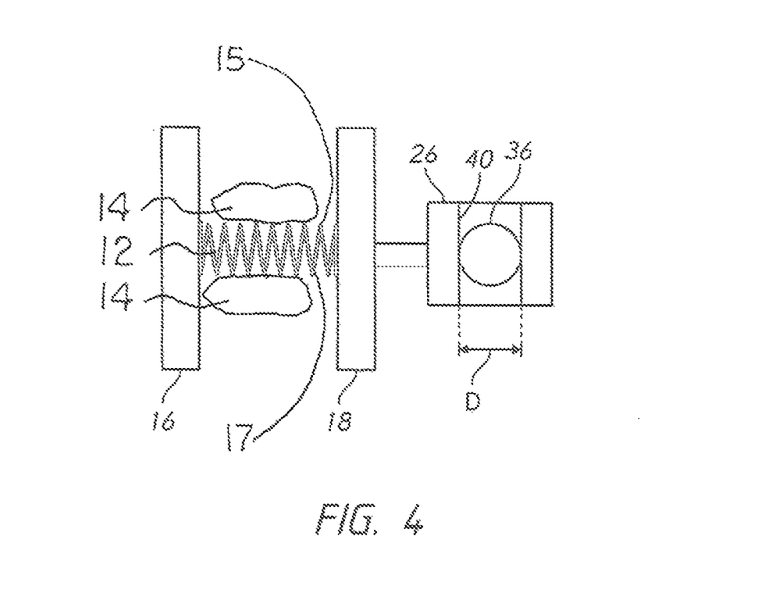
FIG. 4 is a sectional view through one of the fiducial marker holders.

Referring initially to FIG. 3, a bite tray in accordance with the present invention is shown generally designated as 10 for use in making x-ray, CT, or Mill scans of the head. A substantially planar floor 12 is positionable between the upper and lower teeth of a patient when they are clamped together. The floor is typically a nylon mesh for retaining a settable compound 14 such as alginate or vinyl polysiloxane that is added on both sides including the top side 15 and bottom side 17 (FIG. 4) before the tray is inserted into the patient's mouth. An inside teeth perimeter ridge 16 is coupled to the floor for fitting inside the upper and lower teeth of the patient. An outside teeth perimeter ridge 18 is coupled to the floor for fitting outside of the teeth of the patient. A handle 20 facilitates the placement of the bite tray into and out of the mouth of the patient. Fiducial marker holders 22, 24, 26, and 28 are positioned outside of the outside teeth perimeter ridge. Fiducial markers 32, 34, 36, and 38 are located inside. Each holder has a substantially cylindrical aperture 40 with a longitudinal axis 44 substantially perpendicular to the planar floor 12. FIG. 4 is a sectional view along line 4 - 4 of FIG. 3 showing the top side 15 and bottom side 17 retaining setable compound 14 and fiducial marker 36 in the form of a ceramic ball positioned inside the substantially cylindrical aperture 40. Ceramic balls are selected for the fiducial markers because they have a density substantially the same as bone and therefore show on a scan of the bone structure of the head. The preferred diameter D of the aperture is substantially the diameter of a drill bit shank. When a drill bit shank is inserted into an aperture to abut a ceramic ball, it is perpendicular to the plane of the floor of the bit tray and the closed teeth and is used for registering the operating tip to the scan of the head.

Alternatively, any material having a density substantially the same as bone may be used to create the fiducial markers. And they do not have to be spherical so long as the center of the shape can be determined. They may also be affixed to the bite tray by being inlayed or glued to the bite tray instead of in holders. An upper or lower bite tray may also be used instead of a whole tray. The settable compound 14 is then used only on the side that concerns the procedure.

Figure 5:
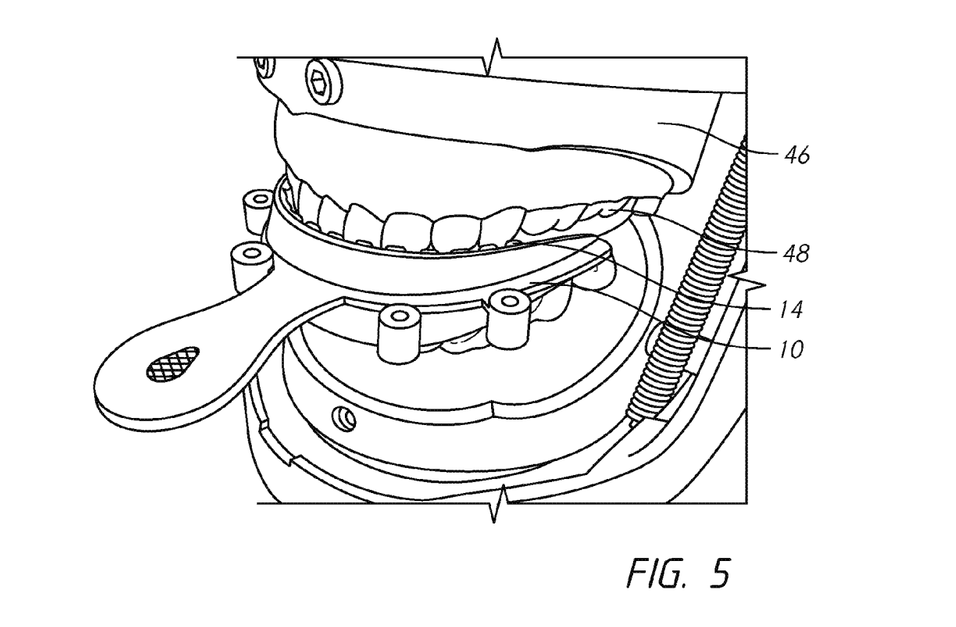
FIG. 5 is perspective view of a patient biting a bite tray making impressions of his teeth in the settable compound.

FIG. 5 is perspective view of a patient 36 biting the bite tray 10 to make impressions of his teeth 38 in the settable compound 14.

Figure 6:
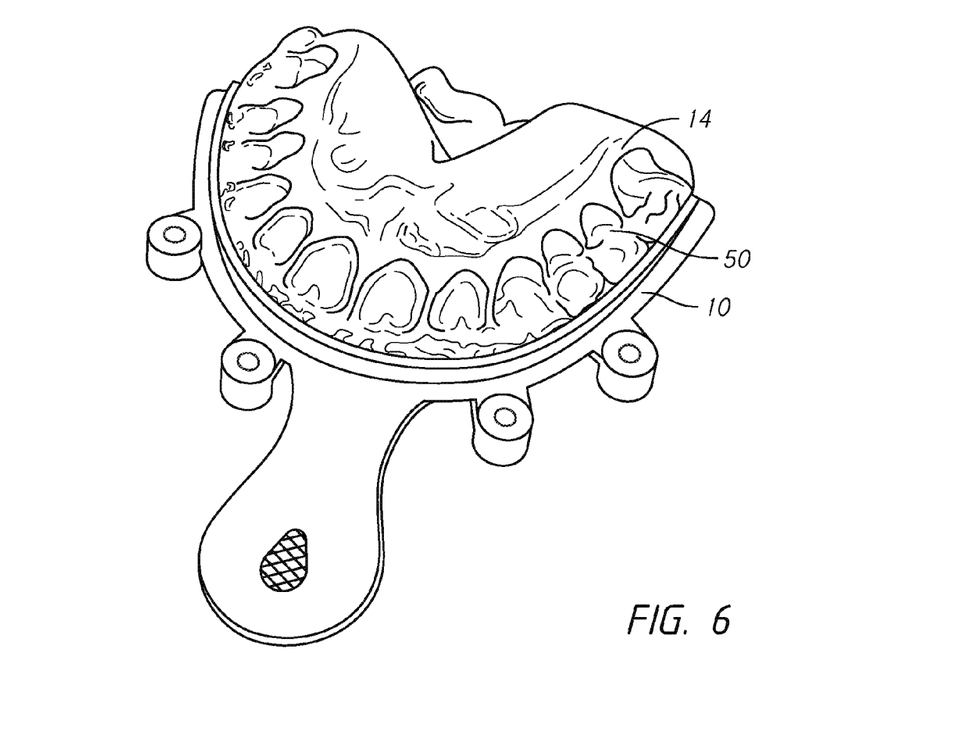
FIG. 6 shows the impressions of the teeth.

FIG. 6 shows the impressions 40 of the teeth in the settable compound 14. The settable compound 14 is then allowed to harden. The bite tray 10 is then reinserted between the teeth of the patient prior to making the x-ray, CT, or MRI scan. The bite tray may also be reinserted between the teeth after a procedure is completed which places the fiducial markers in the same position as before. A new scan can then be made that can be compared to the original scan for checking the results of the procedure.

Figure 7:
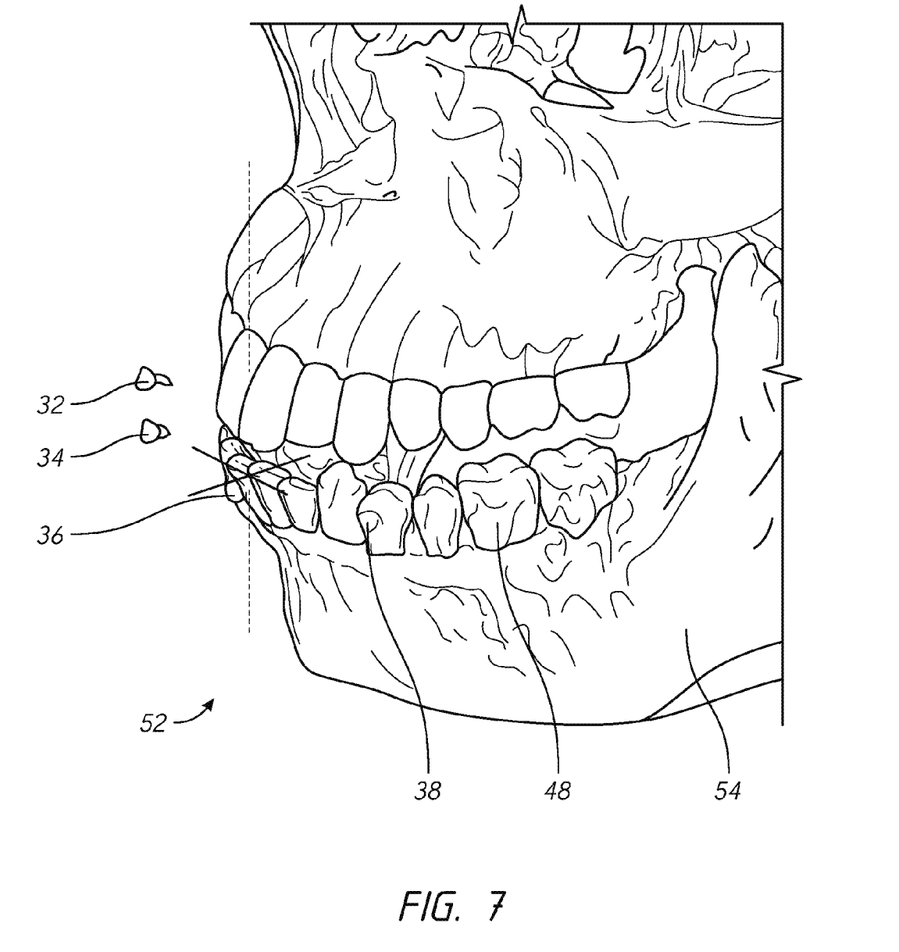
FIG. 7 is a CT or MRI scan image of the head with the bite tray in place showing the fiducial markers.

FIG. 7 is an x-ray, CT or MRI scan image 52 of the head with the bite tray in place between the teeth 48 of the patient showing the fiducial markers 32, 34, 36 and 38. The bite tray does not show because its density is much less than the density of the bones 54 and teeth 48 of the patient. The fiducial markers do show because they are made of ceramic material that has substantially the same density as the bones and teeth of the patient. The fiducial markers markers are further marked on the scan image for better identification.

Figure 8:
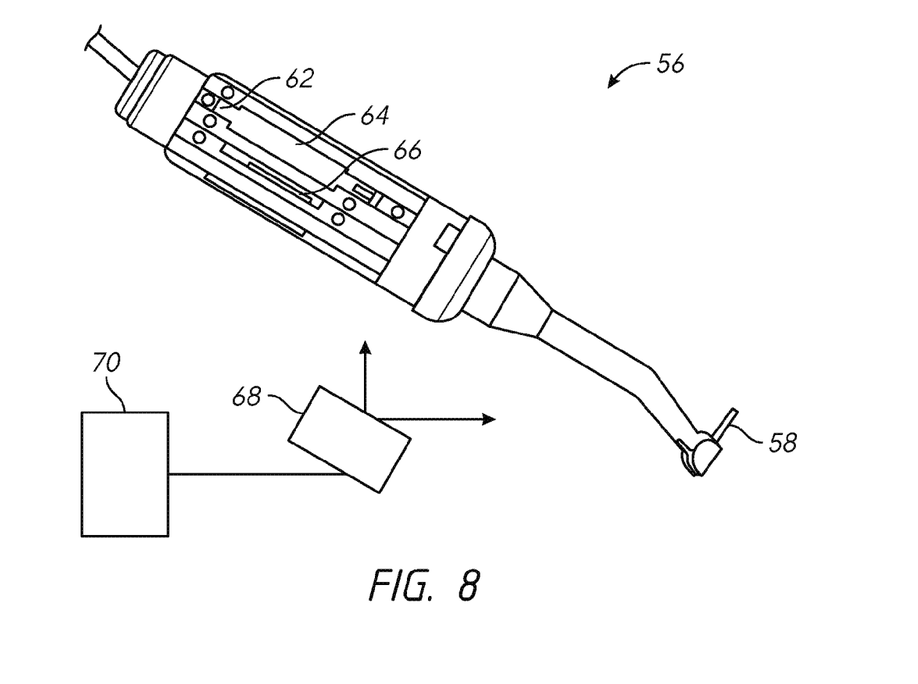
FIG. 8 shows an instrument having an operating tip and instrument markers being observed by a spatial tracking device that delivers the data to a data processing device.

FIG. 8 shows a typical dental instrument 56 having an operating tip 58 and instrument optical markers 62, 64, and 66. A spatial tracking device 68 such as an optical or infrared camera is used for observing the instrument including the operating tip and the instrument optical markers and the overall profile of the instrument. The results of the optical or infrared observation are sent to a data processing device 70 such as a computer.

Figure 9:
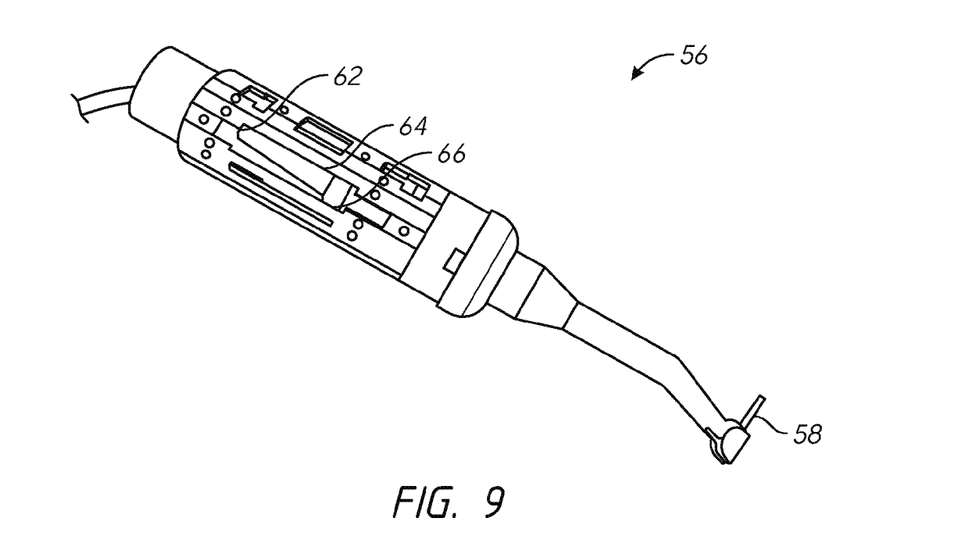
FIG. 9 shows an image of the instrument after it is analyzed by the data processing device.

FIG. 9 shows an image of the instrument 56 created by the data processing device after the instrument is analyzed including the registration of the operating tip 58 to the instrument optical markers 62, 64, and 66. The image is then available to be superimposed on the scan of the head.

Figure 10:
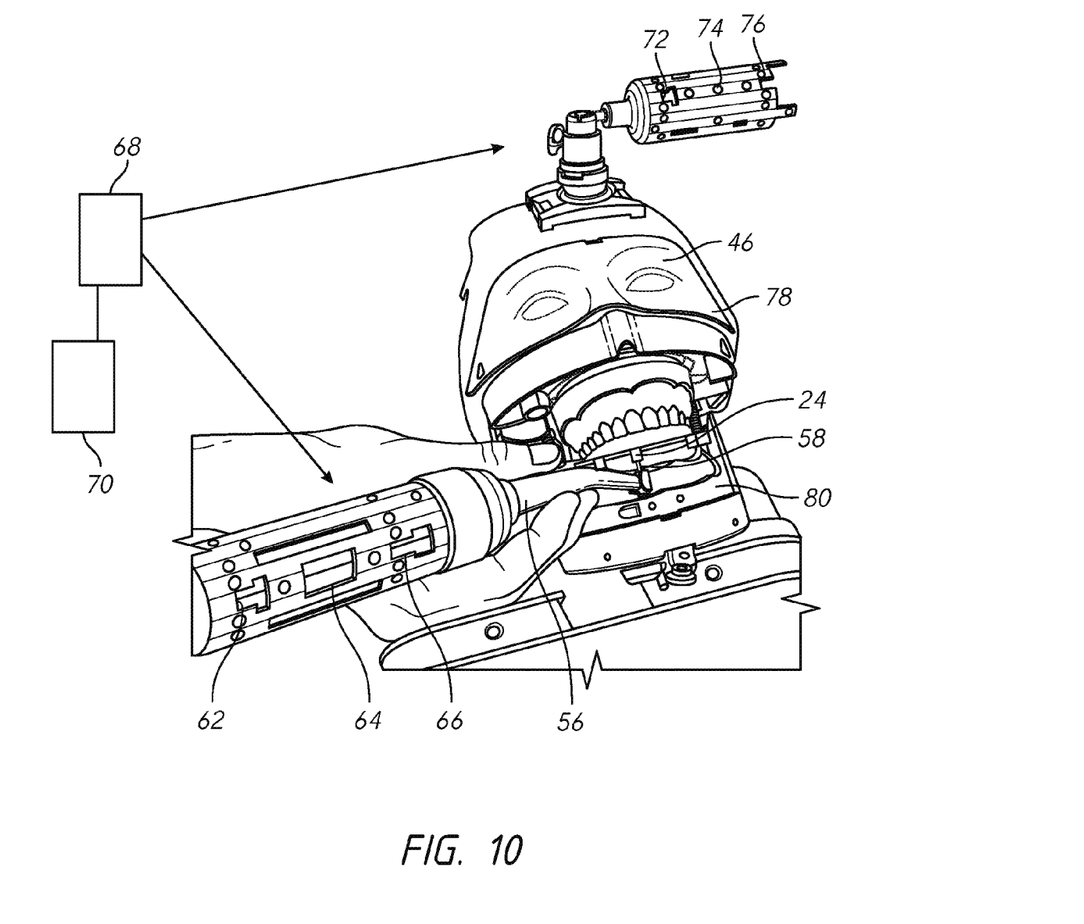
FIG. 10 shows patient markers attached to the head of a patient and the operating tip of the instrument touching a fiducial marker, the spatial tracker observing the instrument optical markers and patient optical markers, and the data transmitted to the data processing device.

FIG. 10 shows patient markers 72, 74, and 76 attached to the top of the head 78 of the patient 46 away from the jaw 80. The patient markers are the reference for the location of the patient in subsequent steps. The operating tip 58 of the instrument 56 is touching the fiducial marker 34 inside a fiducial marker holder 24. The spatial tracking device 68 observes the instrument optical markers 62, 64, and 66 and the patient optical markers 72, 74, 76 at this location and transmits the data to the data processing device 70. At that moment, the relationship of the fiducial marker 34 and the operating tip 58 of the instrument 56 are identical. The data processing device can then compute the registration of the instrument 56 and patient 46 to each other and to the scan image 52. The operating tip of the instrument can also be touched to the other fiducial markers on the bite tray. The spatial tracking device then observes the operating tip, the instrument optical markers, and the patient optical markers at the other locations and transmits the data to the data processing device 70.

Figure 11:
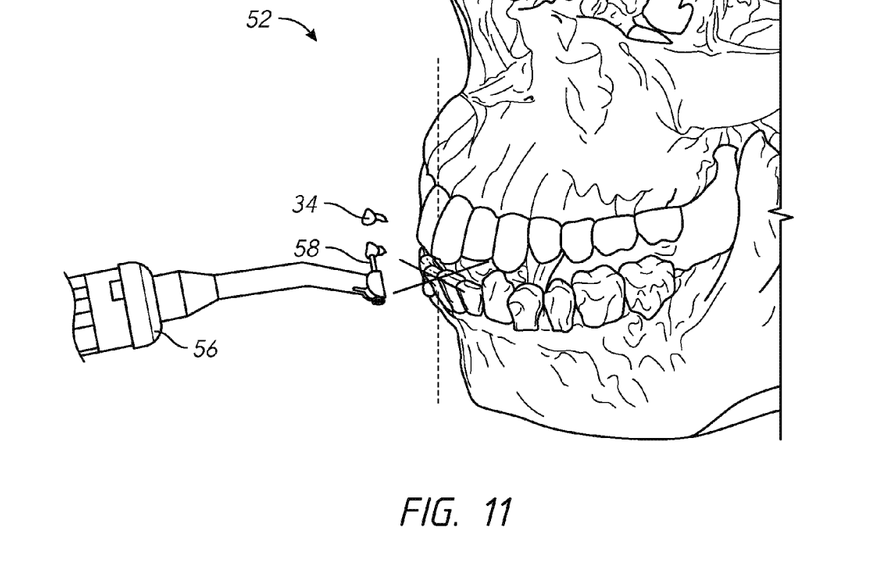
FIG. 11 shows the image of the instrument on the scan image of the head when the operating tip is touching a fiducial marker.

FIG. 11 is a scan image 52 of the head with the operating tip 58 of the instrument 56 superimposed on the scan image when the operating tip touches the fiducial marker 34 in the bite tray.

Figure 12:
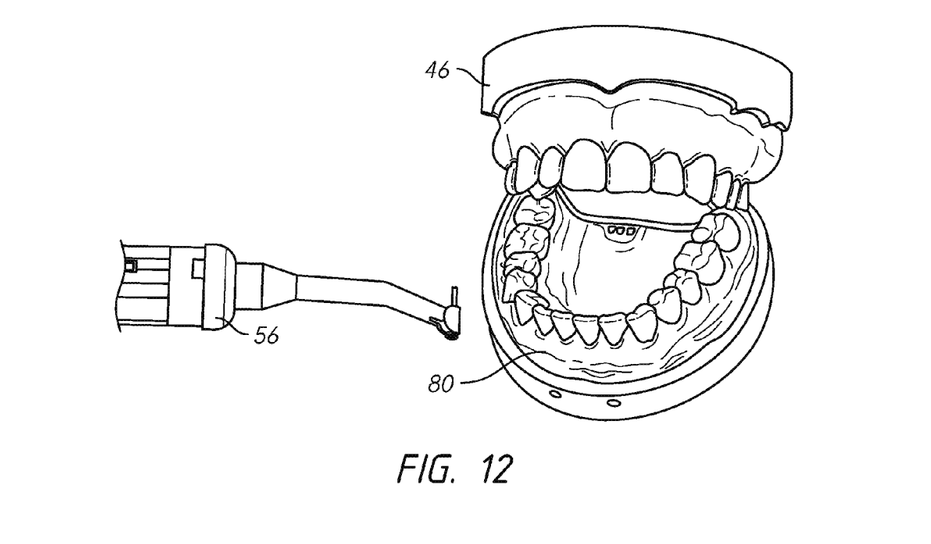
FIG. 12 shows the instrument moved off of the bite tray and the bite tray removed from the patient.

FIG. 12 shows the instrument 56 moved off of the bite tray and the bite tray removed from the jaw 80 of the patient 46.

Figure 13:
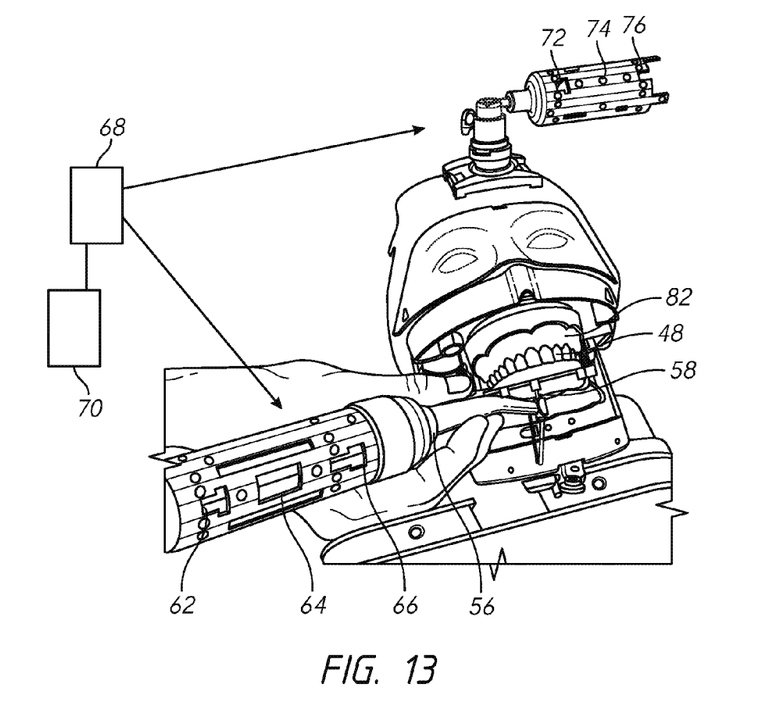
FIG. 13 shows the bite tray removed and the spatial tracking device observing the instrument optical markers and patient optical markers after the operating tip is moved back to the upper jaw and the data delivered to the data processing device.

FIG. 13 shows the operating tip 58 of the dental instrument 56 moved to the upper jaw 82 after the bite tray has been removed. The spatial tracking device 68 observes the instrument optical markers 62, 64, and 66 and the patient optical markers 72, 74, and 76 and delivers the data to the data processing device 70.

Figure 14:
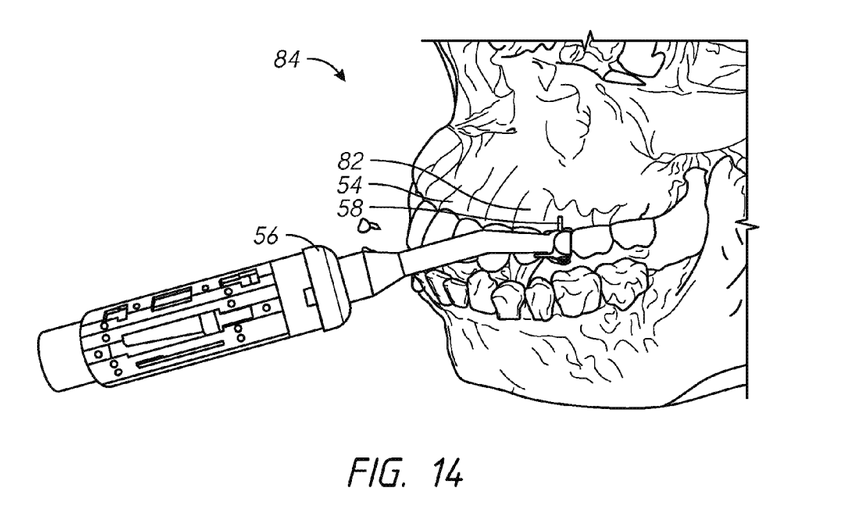
FIG. 14 shows the instrument superimposed on the scan image of the jaw.

FIG. 14 shows the operating image 86 compiled by the data processing device of the arrangement shown in FIG. 13. The instrument 56 and operating tip 58 are superimposed on the previously stored scan image 52. The operating tip 58 is adjacent the upper jaw 82. As the oral surgeon moves the operating tip 58, the process is tracked in real time by the spatial tracking device observing the instrument optical markers (FIG. 13) and the results are posted on the operating image 86 enabling the oral surgeon to see exactly what the operating tip 48 is doing in relation to the bone 44 of the upper jaw.

Figure 15:
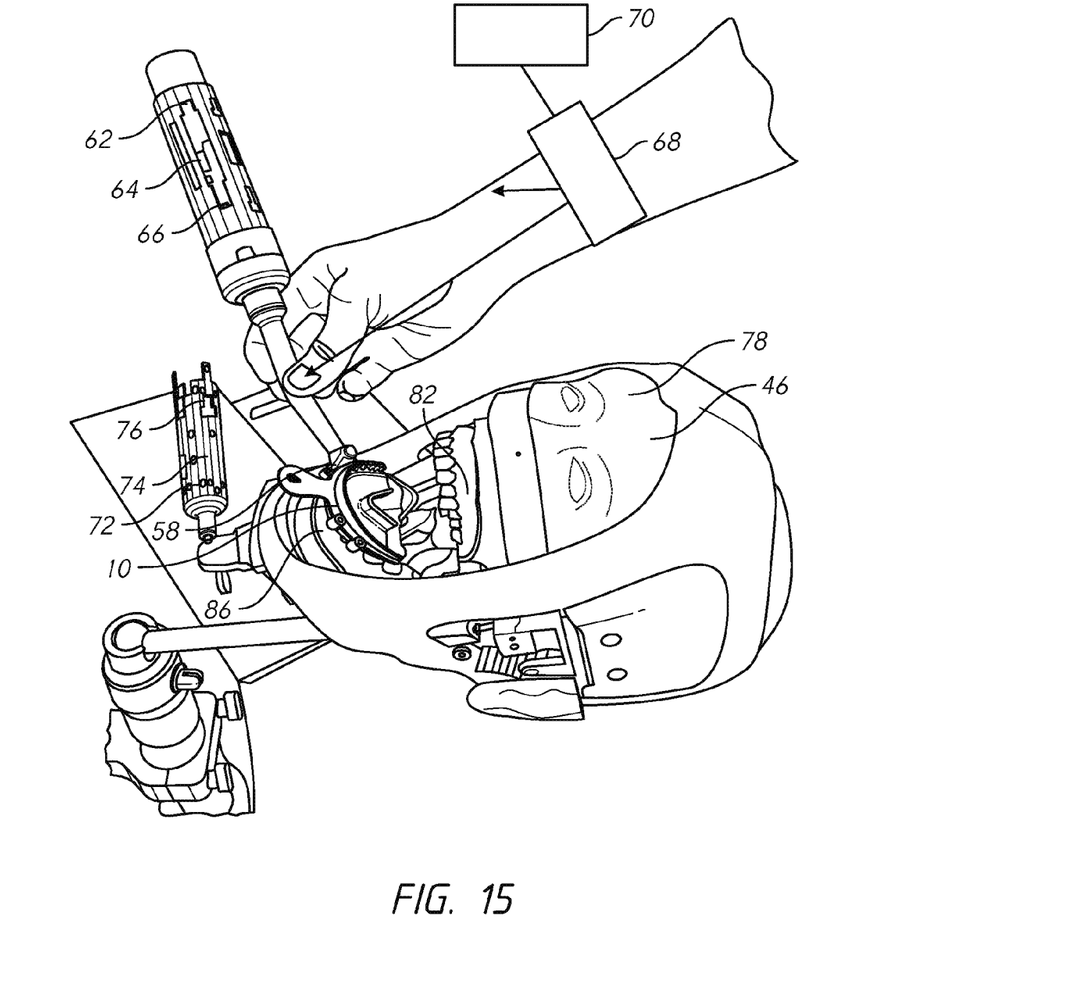
FIG. 15 shows the patient optical markers attached to the lower jaw of the patient and the operating tip of the instrument touching a fiducial marker, the spatial tracking device observing the instrument optical markers and patient optical markers, and the data transmitted to the data processing device.

FIG. 15 is similar to FIG. 13 but shows the arrangement when the oral surgeon is performing a procedure on the lower jaw 86 instead of the upper jaw 82 of the head 78. The patient optical markers 72, 74, and 76 are mounted on the lower jaw because the lower jaw is moved down for procedures on the lower jaw. Before the position shown in FIG. 15, the patient 46 has compressed the bite tray 10 in the manner shown in FIG. 5 and then lowered his jaw to the position shown in FIG. 15 with the bite tray remaining on the lower teeth. A scan image is then made with the lower jaw and bite tray in this position creating a scan image like the scan image shown in FIG. 7 but with the lower jaw lowered. The spatial tracking device 68 observes the instrument optical markers 62, 64, and 66 and patient optical markers 72, 74, and 76 in this position and delivers the data to the data processing device 70. The data processing device compiles an operating image like operating image 84 shown in FIG. 14 but with the lower jaw lowered. The operating tip 58 is touched to one or more of the fiducial markers in the bit tray 10 to register the instrument and patient to the scan image in the same manner as discussed above with respect to procedures on the upper jaw.

Figure 16:
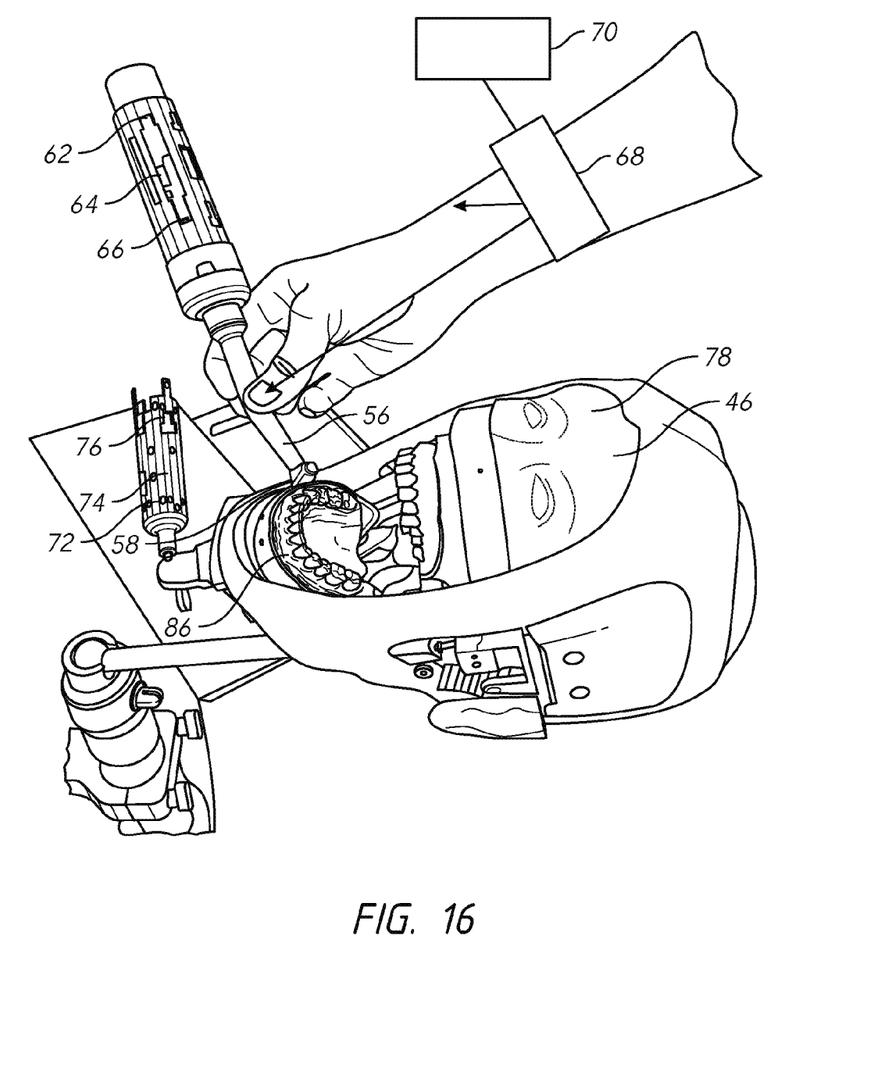
FIG. 16 shows the bite tray removed and the spatial tracking device observing the instrument optical markers and patient optical markers after the operating tip is moved back to the lower jaw and the data delivered to the data processing device.
Figure 17:
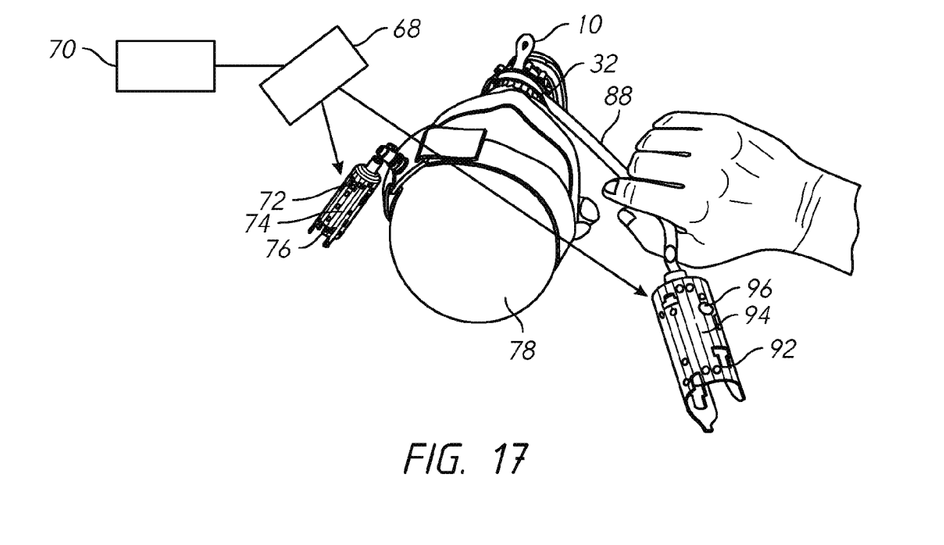
FIG. 17 shows the patient optical markers attached to the side of the head of the patient and the operating tip of the instrument touching a fiducial marker, the spatial tracking device observing the instrument optical markers and patient optical markers, and the data transmitted to the data processing device.

FIG. 16 shows the operating tip 58 of the dental instrument 56 moved to the lower jaw 86 after the bite tray has been removed. The spatial tracking device 68 observes the instrument optical markers 62, 64, and 66 and the patient optical markers 72, 74, and 76 and delivers the data to the data processing device 70. The data processing device creates an operating image similar to the operating image 84 shown in FIG. 14 but on the lower jaw. The operating surgeon can then monitor his procedure on the lower jaw in real time as it progresses FIG. 17 shows the patient optical markers 72, 74, and 76 attached to the side of the head 78 for performing a procedure on the head. A scan image 52 of the head 78 has previously been made as describe in conjunction with FIGS. 3-7. With spatial tracking device 68 observing the procedure as described above, a medical instrument 88 such as a craniotome having medical instrument optical markers 92, 94, and 96 touches fiducial marker 32 in the bite tray 10. The spatial tracking device observes the moment of touching and location of the patient optical markers 72, 74, and 76 and instrument optical markers 92, 94, and 96 and sends the data to the data processing device 70.

Figure 18:
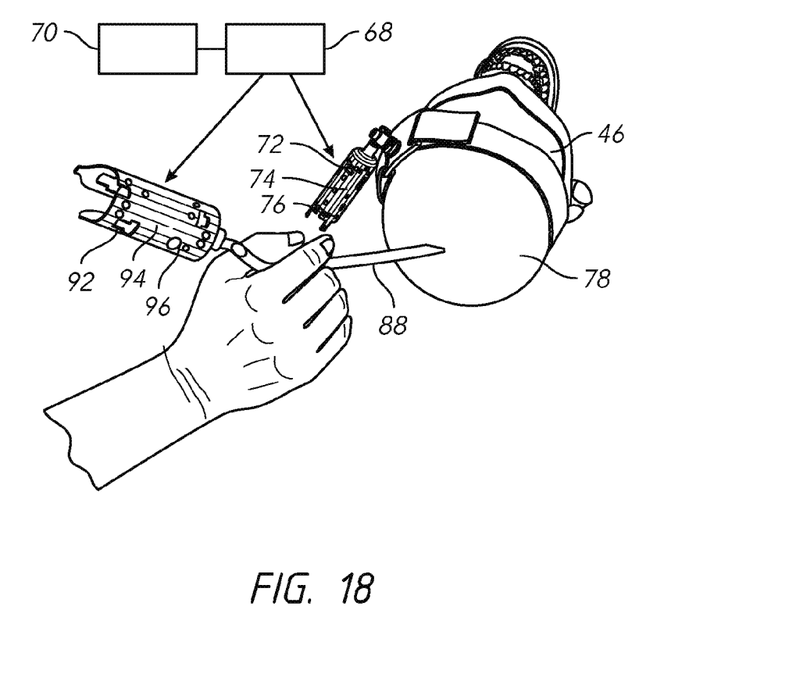
FIG. 18 shows the bite tray removed and the spatial tracking device observing the instrument optical markers and patient optical markers after the operating tip is moved to the top of the head for performing a procedure on the head and the data delivered to the data processing device; and, FIG. 19 shows magnetic instrument markers mounted near the operating end of an instrument and magnetic sensors mounted on a patient.

FIG. 18 shows the bite tray removed. The patient can then open his jaw for insertion of instruments into the mouth or anesthesia apparatus over the nose and mouth. The medical instrument 88 is moved to the top of the head for performing a procedure on the head. A typical use would be to create a burr hole for the insertion of an external ventricular drain. Exact positioning is absolutely necessary to avoid injury to the brain. The process for guiding the instrument 88 on the head is the same as the process for guiding an instrument on the jaw. The spatial tracking device 68 observes the instrument optical markers 92, 94, and 96 and patient optical markers 72, 74, and 76 and sends the data to the data processing device . The data processing device creates an image of the medical instrument 88 superimposed on the scan image of the head in the same manner as described above in conjunction with FIG. 14. The surgeon is then able to monitor the procedure in real time on a display.

Figure 19:
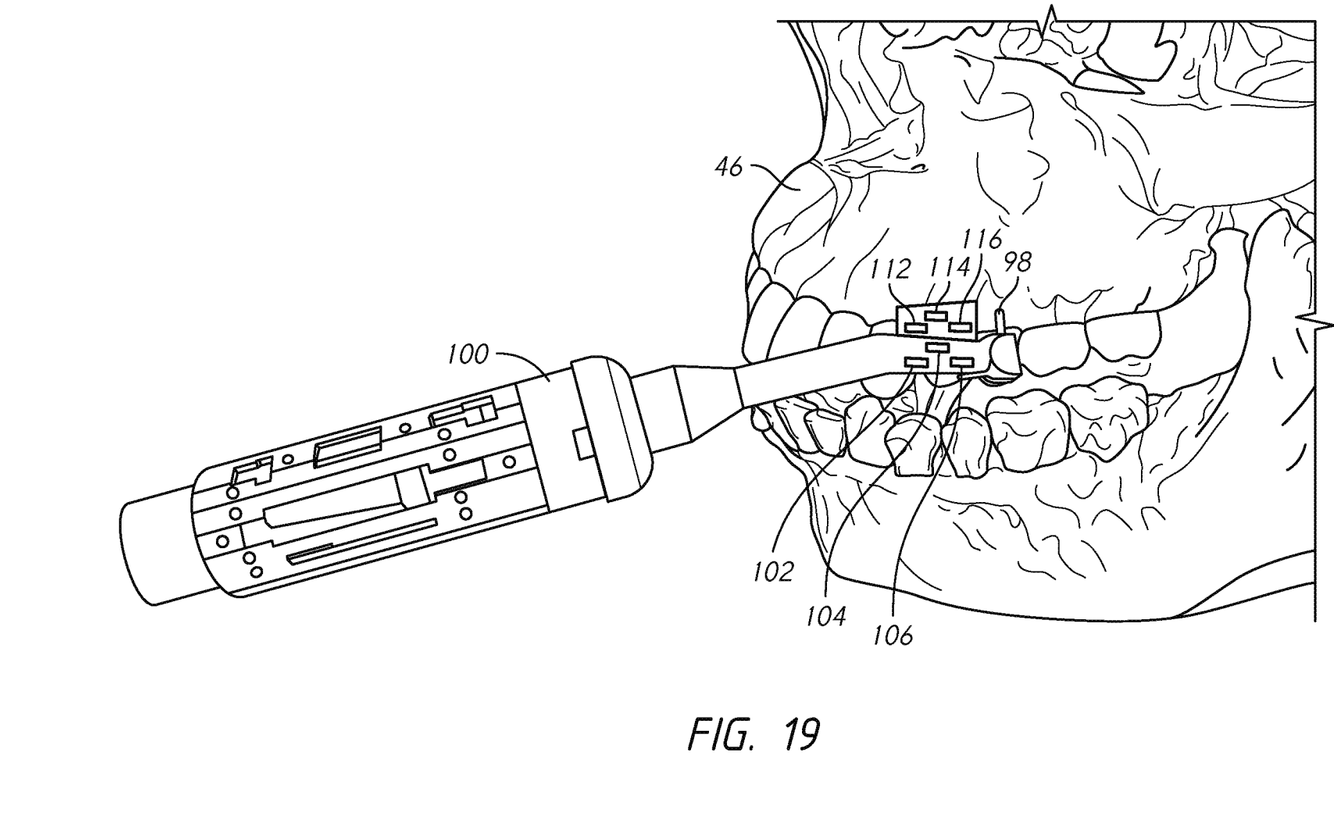

FIG. 19 shows magnetic markers being used instead of optical markers. Magnetic instrument markers 102, 104, and 106 are mounted near the operating tip 98 of a magnetic dental instrument 100 and magnetic sensors 112, 114, and 116 are mounted on a patient 46 near where the procedure is to be performed. The magnetic markers perform the same function as the optical markers of the previous embodiment. After the x-ray, CT, or MRI scan image is made with a bite tray, the magnetic sensors are attached to the patient near where the procedure is to be performed and the operating tip 98 of the instrument 100 is used to touch a fiducial marker on the bite tray as described above in conjunction with FIGS. 13 and 14 to register the scan image, instrument, and patient to each other. The bite tray is then removed and the procedure continues with the relationship of the magnet instrument markers 102, 104, and 106 and the magnetic sensors 112, 114, and 116 to each other providing data to the data processing device. The data processing device in turn creates the image of the instrument 100 superimposed on the scan image as describe and shown in FIG. 14.

The embodiments of the bite tray as a registration device and method of use described herein are exemplary and numerous modifications, combinations, variations, and rearrangements can be readily envisioned to achieve an equivalent result, all of which are intended to be embraced within the scope of the appended claims. Further, nothing in the above provided discussions of the registration device and method should be construed as limiting the invention to a particular embodiment or combination of embodiments. The scope of the invention is defined by the appended claims.

We claim:

1. A bite tray for making x-ray, CT, and MM scans of a head of a patient, comprising:

a floor having a top side and a bottom side adapted for fitting between the upper and lower teeth of the patient when the upper and lower teeth are clamped together;

an inside teeth perimeter ridge coupled to the floor adapted for fitting inside of the upper and lower teeth of the patient when the upper and lower teeth are clamped together;

an outside teeth perimeter ridge coupled to the floor adapted for fitting outside of the upper and lower teeth of the patient when the upper and lower teeth are clamped together;

at least three fiducial markers positioned outside of the outside teeth perimeter ridge; and, a settable compound in the bite tray on the top side and the bottom side of the floor and the upper and lower teeth making impressions of the teeth in the settable compound when the teeth are clamped together;

at least three fiducial marker holders positioned outside of the outside teeth perimeter ridge and a fiducial marker positioned inside each of the holders wherein each of the at least three fiducial markers is a ceramic sphere; and, a drill bit shank having a diameter and an operating tip, wherein the floor is substantially planar, each of the holders has a cylindrical aperture, the cylindrical aperture has a longitudinal axis and is the diameter of the drill bit shank, the longitudinal axis of the cylindrical aperture is perpendicular to the floor, the ceramic sphere is located inside the cylindrical aperture, and the drill bit shank is located inside the cylindrical aperture with its operating tip touching the ceramic sphere, whereby when the drill bit shank is positioned in the cylindrical aperture of a holder with its operating tip touching the ceramic sphere, it is perpendicular to the plane of the floor of the bite tray and the teeth clamped together when in use with the settable compound, the position of the operating tip and drill bit shank are known in relation to the teeth clamped together when in use with the settable compound for registering the positions of the operating tip and drill bit shank of an instrument to a scan of the patient's head.

* * * * *